United States Patent [19]

Hermes et al.

[11] Patent Number: 5,037,429

[45] Date of Patent: Aug. 6, 1991

[54] METHOD FOR IMPROVING THE STORAGE STABILITY OF A POLYMERIC BRAIDED SUTURE SUSCEPTIBLE TO HYDROLYTIC DEGRADATION AND RESULTING ARTICLE

[75] Inventors: Matthew E. Hermes, Easton; Donald S. Kaplan, Weston, both of Conn.

[73] Assignee: United States Surgical Corporation, Norwalk, Conn.

[21] Appl. No.: 529,740

[22] Filed: May 22, 1990

Related U.S. Application Data

[63] Continuation of Ser. No. 89,735, Aug. 26, 1987, abandoned.

[51] Int. Cl.$^5$ .............................................. A61L 17/00
[52] U.S. Cl. ...................................... 606/230; 424/78; 424/447; 524/310; 524/317; 524/354; 524/377; 524/378; 524/386; 524/387; 524/389; 606/231
[58] Field of Search ............... 524/391, 378, 377, 386, 524/387, 310, 317, 354, 910, 911, 389; 424/78, 447; 128/335.5; 435/1, 241; 606/230, 154, 231

[56] References Cited

U.S. PATENT DOCUMENTS

| | | | |
|---|---|---|---|
| 3,009,893 | 11/1961 | Barnes | 524/387 |
| 3,297,033 | 1/1967 | Schmitt et al. | 606/230 |
| 3,531,561 | 9/1970 | Trehu | 264/210 |
| 3,626,948 | 12/1971 | Glick et al. | |
| 3,636,956 | 1/1972 | Schneider | 606/230 |
| 3,728,839 | 2/1973 | Glick | |
| 3,772,420 | 11/1973 | Glick et al. | |
| 3,839,500 | 10/1974 | Dexter | 524/391 |
| 3,839,524 | 10/1974 | Adams et al. | 606/231 |
| 3,849,185 | 11/1974 | Shepherd et al. | 606/231 |
| 3,896,814 | 7/1975 | Vivien et al. | |
| 3,917,740 | 11/1975 | Siclari et al. | 524/910 |
| 4,014,433 | 3/1977 | Cerwin | 606/154 |
| 4,027,676 | 6/1977 | Mattei | 606/231 |
| 4,052,988 | 10/1977 | Doddi et al. | 606/231 |
| 4,081,493 | 3/1978 | Kazama et al. | 524/387 |
| 4,135,622 | 1/1979 | Glick | |
| 4,141,087 | 2/1979 | Shalaby et al. | 606/231 |
| 4,162,242 | 7/1979 | House | 524/387 |
| 4,206,101 | 6/1980 | Wysong | 524/377 |
| 4,330,338 | 5/1982 | Banker | 524/377 |
| 4,363,319 | 12/1982 | Altshuler | 424/447 |
| 4,444,927 | 4/1984 | Borysko | 524/354 |
| 4,466,431 | 8/1984 | Tharrat et al. | 424/447 |
| 4,469,837 | 9/1984 | Cattaneo | 524/387 |
| 4,523,591 | 6/1985 | Kaplan et al. | |
| 4,579,731 | 4/1986 | Fox et al. | 424/447 |
| 4,588,400 | 5/1986 | Ring et al. | 424/447 |
| 4,588,583 | 5/1986 | Pietsch et al. | 524/377 |
| 4,594,240 | 6/1986 | Kawata et al. | 424/447 |
| 4,595,713 | 6/1986 | St. John | 528/354 |
| 4,600,743 | 7/1986 | Shizuki et al. | 524/377 |
| 4,620,974 | 11/1986 | Hersh et al. | 424/78 |
| 4,624,256 | 11/1986 | Messier et al. | 606/231 |
| 4,649,920 | 3/1987 | Rhum | 128/335.5 |
| 4,653,497 | 3/1987 | Bezwada et al. | 606/230 |
| 4,705,820 | 11/1987 | Wang et al. | 606/230 |

*Primary Examiner*—Veronica P. Hoke
*Attorney, Agent, or Firm*—Thomas R. Bremer; Peter G. Dilworth; Rocco S. Barrese

[57] ABSTRACT

The storage stability of a polymeric article susceptible to hydrolytic degradation, e.g., an absorbable suture manufactured from a polymer of glycolic acid, glycolide, lactic acid, lactide or combination thereof, is improved by applying a storage stabilizing amount of at least one water soluble hygroscopic polyhydroxy compound and/or ester thereof, e.g., glycerol, monoacetin, diacetin, and the like, to the article as storage stabilizing agent, said agent being retained by the article prior to sealing of the enclosure in which the suture is packaged.

22 Claims, No Drawings

METHOD FOR IMPROVING THE STORAGE STABILITY OF A POLYMERIC BRAIDED SUTURE SUSCEPTIBLE TO HYDROLYTIC DEGRADATION AND RESULTING ARTICLE

This is a continuation of application Ser. No. 089,735, filed on Aug. 26, 1987, now abandoned.

BACKGROUND OF THE INVENTION

This invention provides a method for improving the storage stability of polymeric articles having an inherent tendency to undergo degradation when exposed to water or a humid atmosphere, probably as a result of hydrolysis. More particularly, the invention is directed to improving the storage stability of articles and devices such as absorbable surgical sutures, clips, staples, implants, prostheses and the like, fabricated from polymers which are susceptible to hydrolytic degradation, notably, polymers and copolymers of glycolic acid (i.e., hydroxyacetic acid), the cyclic dimer of glycolic acid ("glycolide"), lactic acid, the cyclic dimer of lactic acid ("lactide") and related monomers.

Polymers and copolymers of the foregoing kind and absorbable surgical devices made therefrom are well known. See, e.g., U.S. Pat. Nos. 2,668,162; 2,703,316; 2,758,987; 3,225,766; 3,297,033; 3,422,181; 3,531,561; 3,565,869; 3,620,218; 3,626,948; 3,636,956; 3,736,646; 3,772,420; 3,773,919; 3,792,010; 3,797,499; 3,839,297; 3,867,190; 3,878,284; 3,982,543; 4,060,089; 4,137,921; 4,157,437; 4,234,775; 4,237,920; 4,300,565; and, 4,523,591; U.K. Patent No. 779,291; D. K. Gilding et al., "Biodegradable polymers for use in surgery—polyglycolic/poly(lactic acid) homo- and co-polymers: 1, *Polymer,* Volume 20, pages 1459–1464 (1979), and D. F. Williams (ed.), *Biocompatibility of Clinical Implant Materials,* Vol. II, ch. 9: "Biodegradable Polymers" (1981). The biodegradability of these polymers/copolymers is believed to be due to the hydrolytic attack of their ester linkages by aqueous body fluids although the exact mechanism involved has been a matter of speculation.

An absorbable suture (or other aqueous body fluid-absorbable article) may experience prolonged storage before use, e.g., periods of several months and sometimes even several years. In order to prevent water or humidity in the storage environment from contacting the suture and compromising its in vivo strength to the point where the suture is no longer serviceable, it is common practice to package the suture in an essentially moisture impermeable enclosure. However as noted in U.S. Pat. Nos. 3,728,839 and 4,135,622, any package material which prevents the entry of moisture will also prevent the escape of moisture Thus, any moisture associated with or absorbed by the suture at the time it is packaged will tend to remain in the package for the entire period of its storage.

According to aforesaid U.S. Pat. Nos. 3,728,839 and 4,135,622, the in-vivo strength of polyglycolic acid surgical elements such as sutures undergoes significant deterioration on long term standing in the package even on exposure of the contents to very small amounts of water for very short periods of time, e.g., 20 minutes or less, just prior to packaging due to the aforenoted tendency of a moisture impervious package to seal the moisture in with the suture.

To prevent hydrolytic degradation of the suture or to minimize its extent, U.S. Pat. Nos. 3,728,839 and 4,135,622 disclose removing moisture from the suture before sealing the package so that no more than about 0.5 percent of water by weight of suture remains in the package once the package is sealed. This approach to improving the suture's storage stability, while effective, is in practice difficult and expensive to carry out. Prior to sealing the suture within its moisture impervious package, it is essential that the suture be "bone dry", a condition achieved by heating the suture for a sufficient period to remove the water therefrom, e.g., 180°–188° for 1 hour under a 26 inch vacuum. However, once the water is removed, the suture cannot be allowed to contact a moisture-containing environment even for a limited duration since as previously noted, even brief exposure to moisture can cause severe deterioration of suture in vivo strength. It therefore becomes necessary following the water removal step to temporarily store the suture in a dry area, i.e., an environment which is essentially free of moisture, where the possibility of contact with moisture is largely eliminated.

Considered in their entirety, these operations for improving the storage stability of absorbable sutures and other surgical devices which are susceptible to hydrolytic degradation amount to a time consuming, expensive and relatively complex solution to the storage stability problem.

It is an object of the present invention to overcome the aforenoted disadvantages associated with the storage stabilizing method described in U.S. Pat. Nos. 3,728,839 and 4,135,622.

It is therefore an object of this invention to provide a method for improving the storage stability of a polymeric article susceptible to hydrolysis, e.g., an absorbable surgical article such as a suture based in whole or in part on a polyester polymer or copolymer such as polyglycolic acid, lactide-glycolide copolymer, polydioxanone, polytrimethylene carbonate, their copolymers, etc., which requires neither a diminution of the article's pre-packaged moisture content nor temporary storage of the article in an artificially-maintained bone dry environment prior to completion of the packaging operation.

SUMMARY OF THE INVENTION

In accordance with the present invention, a method is provided for improving the storage stability of a polymeric article susceptible to hydrolysis which comprises applying a storage stabilizing amount of at least one water soluble hygroscopic polyhydroxy compound or ester thereof to the polymeric article as storage stabilizing agent therefor.

Ordinarily, the foregoing method can be carried out upon the polymeric article without the need to reduce its moisture level, either before or after applying the stabilizing agent thereto, to a very low level, e.g., to a state of being bone dry as in U.S. Pat. Nos. 3,728,839 and 4,135,622, since entirely acceptable levels of storage stability can be achieved without resorting to such drastic moisture reduction efforts. Similarly, it is altogether unnecessary to maintain the article in a bone dry environment at any time following its manufacture and preceding the completion of its packaging as in the aforesaid patents. Once the article is contacted with the storage stabilizing agent which will thereafter be retained on and/or within the polymeric article, for example, by adhering to its surfaces and/or being sorbed by the polymeric composition of which the article is constructed, the article can be immediately packaged since all that is necessary to effect its long term hydrolytic stability will have been accomplished by the storage stabilizing agent application operation. Such being the case, the storage stabilizing method of the present invention possesses the advantages of simplicity, economy and a level of production efficiency unattainable by the storage stabilizing method described in U.S. Pat. Nos. 3,728,839 and 4,135,622.

In addition to imparting an enhanced degree of storage stability upon polymeric articles which are subject to hydrolytic degradation, practice of the present invention may confer other benefits as well. So, for example, an absorbable suture which has been filled with a storage stabilizing amount of glycerol in accordance with the method herein has been found to exhibit better flexibility and "hand" characteristics than the untreated suture. Moreover, since the hygroscopic compounds useful in the practice of this invention are generally capable of dissolving a number of medico-surgically useful substances, they can be used as vehicles to deliver such substances to a wound or surgical site at the time the suture (or other absorbable surgical device) is introduced into the body.

The term "filled" as used herein refers to the association of the polymeric article with a storage stabilizing amount of storage stabilizing agent whether this association be one in which the storage stabilizing agent is absorbed by the polymeric article, is present on the surfaces thereof or is a combination of the two.

DESCRIPTION OF THE PREFERRED EMBODIMENTS

A characteristic which the polymeric articles to be contacted with a storage stabilizing agent in accordance with this invention share in common is their relatively high susceptibility to undergoing destructive hydrolysis over a period of storage. Generally, this is an inherent characteristic of polymers and copolymers possessing a significant number of short-chain ester linkages in their structure as, for example, is the case with polyglycolic acid, lactide-glycolide polymers, polydioxanone, polytrimethylene carbonate, their copolymers, and related materials. While the invention is particularly useful for application to absorbable sutures both of the monofilament and multifilament type (e.g., those of the braided variety which are especially hygroscopic) fabricated from polymers and copolymers of this kind, it is applicable to other types of surgically useful articles as well, e.g., those disclosed in U.S. Pat. No. 4,135,622, including without limitation, absorbable surgical clips, staples, sponges, gauze, implants and prostheses for reconstructing bone tissue, blood vessels, and so forth.

The useful storage stabilizing agents are generally selected from the water soluble hygroscopic polyhydroxy compounds or esters of such compounds, preferably those having no appreciable toxicity for the body at the levels present. With these requirements in mind, those skilled in the art are readily capable of identifying any number of storage stabilizing agents useful in the practice of this invention. Among the specific stabilizing agents which can be used herein with generally good results are glycerol and its mono- and diesters derived from low molecular weight carboxylic acids, e.g., monoacetin and diacetin (respectively, glyceryl monoacetate and glyceryl diacetate), ethylene glycol, diethylene glycol, triethylene glycol, 1,3-propanediol, trimethylolethane, trimethylolpropane, pentaerythritol, sorbitol, and the like. Glycerol is especially preferred. Mixtures of storage stabilizing agents, e.g., sorbitol dissolved in glycerol, glycerol combined with monoacetin and/or diacetin, etc., are also useful. If necessary or desirable, the stabilizing agent(s) can be dissolved in any suitable non-aqueous solvent or combination of solvents prior to use. To be suitable, the solvent must (1) be miscible with the storage stabilizing agent at the concentration of the latter, (2) have a sufficiently high vapor pressure to be readily removed by evaporation, (3) not appreciably affect the integrity of the polymeric article and (4) capable, in combination with the storage stabilizing agent, of wetting the surface of the surgical article. Applying these criteria to a preferred storage stabilizing agent, glycerol, lower alcohols such as methanol and ethanol are entirely suitable solvent carriers.

Application of the storage stabilizing agent to the polymeric article can be carried out in any number of ways. Thus, for example, the article can be submerged in the storage stabilizing agent or solution thereof until at least a storage stabilizing amount of agent is acquired or otherwise retained by the article, even after the optional removal of any excess agent and/or accompanying solvent (if present) such as by drainage, wiping, evaporation, etc. In many cases, contact times on the order of from just a few seconds, e.g., about 10 seconds or so, to several hours, e.g., about 2 hours and even longer, are sufficient to impart a substantial improvement in the storage stability of the treated article compared to the same type of article which has not been treated with a storage stabilizing agent.

The foregoing submersion method of contacting the polymeric article with storage stabilizing agent can be conducted continuously or in batch. Thus, in the case of an absorbable suture, a running length of the suture can be continuously passed through a quantity of the stabilizing agent at a velocity which has been previously determined to provide the necessary degree of exposure, or contact time, of the suture with the storage stabilizing agent. As the suture emerges from the storage stabilizing agent, it can be passed through a wiper or similar device to remove excess agent prior to the packaging operation. In a batch operation, a quantity of suture is merely submerged within the storage stabilizing agent for the requisite period of time with any excess agent being removed from the suture if desired.

Alternatively, the storage stabilizing agent and solutions thereof can be applied by spraying, brushing, wiping, etc., on the surfaces of the polymeric articles such that the latter receive and retain at least a storage stabilizing amount of the agent. Yet another procedure which can be used to apply the storage stabilizing agent involves inserting the polymeric article in a package containing an effective amount of the agent such that intimate contact between the polymeric article and the agent will be achieved.

Whatever the contacting procedure employed, it is necessary that the article being treated acquire a storage stabilizing amount of the storage stabilizing agent. In general amounts of from about 2 to about 25, and preferably from about 5 to about 15 weight percent, of storage stabilizing agent(s) (exclusive of any solvent) by weight of the polymeric article contacted therewith is sufficient to provide significantly improved storage stability compared to that of the untreated article.

The method of the invention can be practiced in conjunction with other known and conventional procedures such as sterilization. Known and conventional packaging techniques and materials are also contemplated. As previously stated, an advantage of the present invention lies in its ability to provide enhanced storage stability in a polymeric article susceptible to hydrolytic degradation without having to eliminate all but a small amount of moisture from the article and maintain the article in an especially dry environment until the final package sealing operation as disclosed in U.S. Pat. Nos. 3,728,839 and 4,135,622. While the present invention can be practiced with a suture or other article which has been treated in this manner, there is no necessity of doing so and for reasons of simplicity, economy and production efficiency, it is preferred that the article to be contacted with storage stabilizing agent in accordance with this invention not receive the treatment described in the aforesaid patents.

It is preferred that the method of this invention be practiced upon a polymeric article whose moisture level has equilibrated to that of the surrounding atmosphere, e.g., from about 5 percent to about 40 percent relative humidity or even higher. Such a moisture content in the atmosphere will typically result in a stabilized surgical article possessing an amount of moisture in the range of from about 0.3 to about 1.0 weight percent or more. Moisture levels within this range, while not tolerated by the packaging method and packaged synthetic surgical element of U.S. Pat. Nos. 3,728,839 and 4,135,622, have no appreciably deleterious effect on the long term in vivo strength of polymeric articles contacted with a storage stabilizing agent in accordance with the present invention. Thus, the polymeric article treated with storage stabilizing agent can, if desired, be packaged at relatively high levels of relative humidity, e.g., those just mentioned.

It can be advantageous to apply one or more coating compositions to the storage stabilized article of this invention where particular functional properties are desired. Thus, for example, in the case of an absorbable suture which has been treated with glycerol for improved long term storage, the storage stabilized article can be coated with a polyethylene oxide-polypropylene oxide block copolymer or polyalkylene glycol, either of which has been further polymerized with glycolide monomer and lactide monomer or glycolide/lactide copolymer to improve surface lubricity and facilitate knot tie-down as disclosed in commonly assigned U.S. patent application Ser. Nos. 089,733 and 089,734, filed concurrently herewith, all now abandoned.

As previously noted, it can be advantageous to employ the storage stabilizing agent as a carrier for one or more medico-surgically useful substances, e.g., those which accelerate or otherwise beneficially modify the healing process when applied to a wound or surgical site. In general, any biologically active material which is soluble in and otherwise compatible with the selected storage stabilizing agent can be incorporated therein in therapeutically useful amounts. So, for example, a suture can be filled with storage stabilizing agent containing a therapeutic agent which will be deposited at the sutured site. The therapeutic agent may be chosen for its antimicrobial properties, capability for promoting wound repair and/or tissue growth or for specific indications such as thrombolysis. Antimicrobial agents such as broad spectrum antibiotics (gentamycin sulphate, erythromycin or derivatized glycopeptides) which are slowly released into the tissue can be applied in this manner to aid in combating clinical and sub-clinical infections in a surgical or trauma wound site. To promote wound repair and/or tissue growth, one or several growth promoting factors can be added to the storage stabilizing agent, e.g., fibroblast growth factor, bone growth factor, epidermal growth factor, platelet derived growth factor, macrophage derived growth factor, alveolar derived growth factor, monocyte derived growth factor, magainin, and so forth. Some therapeutic indications are: glycerol with tissue or kidney plasminogen activator to cause thrombolysis, superoxide dismutase to scavenge tissue damaging free radicals, tumor necrosis factor for cancer therapy or colony stimulating factor and interferon, interleukin-2 or other lymphokine to enhance the immune system.

The following examples are illustrative of the storage stabilizing method and storage stabilized polymeric article of this invention.

EXAMPLES 1-5

In the following examples, five specimens of absorbable suture were prepared, packaged, sealed and maintained under accelerated storage conditions and tested for in vitro strength (U.S.P. Knot Pull Test) as follows:

| Example | Absorbable Suture | Moisture Content at Packaging (wt. %) | Percent Relative Humidity at Packaging | Glycerol Storage Stabilizing Agent (wt. %) |
|---|---|---|---|---|
| 1 (control) | VICRYL[1] | ≤0.05 | — | — |
| 2 | VICRYL cleaned[2] | 0.3 | 6 | 10 |
| 3 | VICRYL cleaned[2] | 1.0 | 40 | 10 |
| 4 (control) | VICRYL[3] | 0.22 | 6 | — |
| 5 (control) | VICRYL[3] | 0.38 | 40 | — |

[1]VICRYL (Ethicon, Inc.) is a braided absorbable suture believed to be fabricated from a copolymer derived from 90 mole percent glycolide and 10 mole percent lactide. As packaged, the suture is coated with a lubricant in order to improve knot tie-down properties. Size 1-0 was used in these evaluations.
[2]VICRYL suture from which the original coating has been substantially removed.
[3]VICRYL suture packages were opened then resealed after equilibrating at the relative humidity shown.

To simulate the effects of long term storage on in vivo strength, the packaged sutures were stored for the periods designated in the table below at 132° F. and 10 percent relative humidity.

Simulating in vivo strength, the sutures were placed in 98.6° F. buffered saline. The results of the Knot Pull test were as follows:

TABLE 1

| Results of In Vitro Strength Following Accelerated Storage | | | | |
|---|---|---|---|---|
| Example 1 | Example 2 | Example 3 | Example 4 | Example 5 |

$T_0$ (no storage)

| | | | | |
|---|---|---|---|---|
| $t_0$ 4.9 kg | 5.6 | 5.4 | 4.8 | 5.4 |
| $t_1$ 4.9 kg | 4.0 | 4.9 | 4.3 | 4.1 |
| $t_2$ 3.1 kg | 3.5 | 3.6 | 2.3 | 2.3 |
| $t_3$ 1.3 kg | 1.5 | 1.5 | — | — |

$T_1$ (one week storage)

| | | | | |
|---|---|---|---|---|
| $t_0$ 4.8 kg | 5.2 | 5.0 | 4.3 | 4.3 |
| $t_1$ 4.4 kg | 4.8 | 4.5 | 2.9 | 3.5 |
| $t_2$ 3.1 kg | 3.6 | 2.7 | 1.9 | 1.6 |
| $t_3$ 1.5 kg | 1.7 | 1.1 | — | — |

$T_2$ (two week storage)

| | | | | |
|---|---|---|---|---|
| $t_0$ 5.3 kg | 5.2 | 3.7 | 4.5 | 3.6 |
| $t_1$ 4.6 kg | 5.2 | 4.3 | 1.9 | 3.2 |
| $t_2$ 2.9 kg | 2.2 | 3.0 | 1.4 | 0.6 |
| $t_3$ 2.4 kg | 2.8 | 0.9 | — | — |

$T_3$ (three week storage)

| | | | | |
|---|---|---|---|---|
| $t_0$ 5.5 kg | 6.0 | 3.8 | 4.7 | 3.3 |
| $t_1$ 4.8 kg | 4.7 | 2.8 | 2.1 | 3.2 |
| $t_2$ 2.2 kg | 2.6 | 0.6 | 2.0 | 1.0 |

TABLE 1-continued

Results of In Vitro Strength Following Accelerated Storage

| | Example 1 | Example 2 | Example 3 | Example 4 | Example 5 |
|---|---|---|---|---|---|
| $t_3$ | 1.2 kg | 1.2 | 0.6 | — | — |
| $T_4$ (four week storage) | | | | | |
| $t_0$ | 4.8 kg | 4.8 | 3.8 | 4.4 | 2.8 |
| $t_1$ | 3.8 kg | 4.3 | 1.8 | 2.9 | 1.6 |
| $t_2$ | 2.5 kg | 2.9 | 1.2 | 1.5 | 0.7 |
| $t_3$ | 0.9 kg | 1.4 | 0.4 | — | — |
| $T_6$ (six week storage) | | | | | |
| $t_0$ | 4.9 kg | 4.7 | 3.9 | 4.4 | 2.4 |
| $t_1$ | 3.6 kg | 4.0 | 2.2 | 2.9 | 1.2 |
| $t_2$ | 2.4 kg | 1.9 | 1.2 | 1.3 | 0.5 |

As these data show, despite the moisture content being six times higher for the suture of Example 2 compared to the commercial control sample of Example 1, the measured in vitro strengths of the suture of Example 2 were about as good as, and in some cases exceeded, that of the suture of Example 1. Comparing the data of Example 2 with that of Example 4, it is seen that despite its higher water content, the glycerol-treated suture of this invention retained a significantly higher percentage of its initial in vitro strength compared to the nontreated suture. Even when the suture possesses a moisture content of 1.0 weight percent (Example 3), a level which is double the maximum 0.5 weight percent level tolerated by the suture storage stabilizing method and storage stabilized suture of U.S. Pat. Nos. 3,728,839 and 4,135,622, it possessed much better storage stability than a suture of considerably lower moisture content (Example 5) even though both sutures were packaged in an environment of identical relative humidity.

EXAMPLES 6-7

Specimens of 1-0 Vicryl braided absorbable suture (approximately 0.005 weight percent moisture as originally packaged) which had been stripped of their original coatings were filled with about 10 weight percent glycerol and then coated with a copolymer prepared from equal parts by weight of a polyethylene glycol (molecular weight of about 7500) and a 20/80 glycolide-lactide copolymer in order to enhance the suture's knot run-down and knot tie-down characteristics. The coated suture was then equilibrated at relative humidities of 15 and 20%, respectively, at ambient temperature (Examples 6 and 7). Finally, the suture specimens were subjected to accelerated storage and tested for in vitro strength as in Examples 1-5. The results of the Knot Pull test were as follows:

TABLE 2

Results of In Vitro Strength Following Accelerated Storage

| | Example 6 (0.45 wt. % moisture at packaging) | Example 7 (0.70 wt. % moisture at packaging) |
|---|---|---|
| $T_0$ (no storage) | | |
| $t_0$ | 5.32 | 5.42 |
| $t_1$ | 4.70 | 4.85 |
| $t_2$ | 3.00 | 3.18 |
| $T_2$ (two week storage) | | |
| $t_0$ | 5.16 | 4.98 |
| $t_1$ | 4.7 | 3.75 |
| $t_2$ | 2.7 | 2.3 |
| $T_3$ (three week storage) | | |
| $t_0$ | 4.7 | 4.45 |
| $t_1$ | 3.7 | 3.35 |
| $t_2$ | 1.8 | 1.3 |
| $T_4$ (four week storage) | | |
| $t_0$ | 4.69 | 3.76 |
| $t_1$ | 2.7 | 1.75 |
| $t_2$ | 2.1 | 1.7 |
| $T_6$ (six week storage) | | |
| $t_0$ | 3.8 | 3.1 |
| $t_1$ | 2.73 | 1.34 |
| $t_2$ | 1.62 | 1.06 |

These data further demonstrate the effectiveness of applying glycerol to an absorbable suture in accordance with the present invention to improve the storage stability of the latter.

What is claimed is:

1. A method for improving the storage stability of a bioabsorbable polymeric braided surgical suture fabricated from a polymer susceptible to hydrolysis which comprises applying a storage stabilizing amount of glycerol to a braided surgical suture formed from said polymer.

2. The method of claim 1 wherein said bioabsorbable polymeric braided surgical suture is fabricated in whole or in part from a polymer or copolymer of glycolic acid, glycolide, lactic acid, lactide or combination thereof.

3. The method of claim 1 wherein said glycerol is dissolved in at least one organic solvent therefor.

4. The method of claim 3 wherein the organic solvent is a lower alcohol.

5. The method of claim 1 wherein application of said glycerol is carried out by submerging said bioabsorbable polymeric braided surgical suture in said glycerol.

6. The method of claim 1 wherein application of said glycerol is carried out by coating, spraying or wiping said bioabsorbable polymeric braided surgical suture with said glycerol.

7. The method of claim 1 wherein said bioabsorbable polymeric braided surgical suture possesses a moisture content of greater than about 0.5 weight percent.

8. The method of claim 1 wherein said bioabsorbable polymeric braided surgical suture possesses a moisture content of up to about 1.5 weight percent at the time it is sealed within a substantially moisture impermeable enclosure therefor.

9. The method of claim 1 wherein said bioabsorbable polymeric braided surgical suture retains from about 2 to about 25 weight percent of said glycerol at the time it is sealed within a substantially moisture impermeable enclosure therefor.

10. The method of claim 1 wherein said glycerol contains dissolved therein an effective amount of at least one medico-surgically useful substance.

11. The method of claim 10 wherein said medico-surgically useful substance is tissue growth factor.

12. A method for delivering a medico-surgically useful substance to a wound or surgical site which comprises applying to a bioabsorbable polymeric braided surgical suture fabricated from a polymer susceptible to hydrolysis intended to be contacted with said site, a composition comprising an effective amount of medico-surgically useful substance dissolved in glycerol.

13. The method of claim 12 wherein the medico-surgically useful substance is a tissue growth factor.

14. A bioabsorbable polymeric braided surgical suture fabricated from a polymer which is susceptible to hydrolysis possessing a storage stabilizing amount of glycerol applied to the braided surgical suture formed from said polymer.

15. The bioabsorbable polymeric braided surgical suture of claim 14 fabricated in whole or in part from a polymer or copolymer of glycolic acid, glycolide, lactic acid, lactide or combination thereof.

16. The bioabsorbable polymeric braided surgical suture of claim 14 possessing a moisture content of greater than about 0.05 weight percent.

17. The bioabsorbable braided surgical suture of claim 14 possessing a moisture content of from about 0.3 to about 1.0 weight percent.

18. The bioabsorbable polymeric braided surgical suture of claim 14 possessing from about 2 to about 25 weight percent of said glycerol.

19. The bioabsorbable polymeric braided surgical suture of claim 14 wherein said glycerol contains an effective amount of at least one medico-surgically useful substance dissolved therein.

20. The bioabsorbable polymeric braided surgical suture of claim 19 wherein said medico-surgically useful substance is tissue growth factor.

21. A method of improving the storage stability of a bioabsorbable polymeric braided surgical suture fabricated in whole in or part from a polymer or copolymer susceptible to hydrolysis, said polymer or copolymer comprised of glycolic acid, glycolide, lactic acid, lactide or combinations thereof, which comprises applying a storage stabilizing amount of glycerol to a braided surgical suture formed from said polymer or copolymer.

22. A bioabsorbable polymeric braided surgical suture fabricated in whole or in part from a polymer or copolymer susceptible to hydrolysis, said polymer or copolymer comprised of glycolic acid, glycolide, lactic acid, lactide or combinations thereof possessing a storage stabilizing amount of glycerol applied to the braided surgical suture formed from said polymer or copolymer.

* * * * *